(12) United States Patent
Kitagawa et al.

(10) Patent No.: US 12,246,115 B2
(45) Date of Patent: Mar. 11, 2025

(54) MEDICAL DEVICE AND METHOD OF MANUFACTURING SAME

(71) Applicant: TORAY INDUSTRIES, INC., Tokyo (JP)

(72) Inventors: Rumiko Kitagawa, Otsu (JP); Masataka Nakamura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 936 days.

(21) Appl. No.: 17/289,588

(22) PCT Filed: Dec. 5, 2019

(86) PCT No.: PCT/JP2019/047628
§ 371 (c)(1),
(2) Date: Apr. 28, 2021

(87) PCT Pub. No.: WO2020/121940
PCT Pub. Date: Jun. 18, 2020

(65) Prior Publication Data
US 2022/0008631 A1    Jan. 13, 2022

(30) Foreign Application Priority Data

Dec. 12, 2018   (JP) ................. 2018-232197

(51) Int. Cl.

| | | |
|---|---|---|
| *A61L 31/14* | (2006.01) | |
| *A61F 2/14* | (2006.01) | |
| *A61L 15/24* | (2006.01) | |
| *A61L 15/26* | (2006.01) | |
| *A61L 15/44* | (2006.01) | |
| *A61L 27/18* | (2006.01) | |
| *A61L 27/34* | (2006.01) | |
| *A61L 27/52* | (2006.01) | |
| *A61L 27/54* | (2006.01) | |
| *A61L 29/06* | (2006.01) | |
| *A61L 29/08* | (2006.01) | |
| *A61L 29/14* | (2006.01) | |
| *A61L 29/16* | (2006.01) | |
| *A61L 31/10* | (2006.01) | |
| *A61L 31/16* | (2006.01) | |
| *C08G 77/20* | (2006.01) | |

(Continued)

(52) U.S. Cl.
CPC ............. *A61L 31/145* (2013.01); *A61L 15/24* (2013.01); *A61L 15/26* (2013.01); *A61L 15/44* (2013.01); *A61L 27/18* (2013.01); *A61L 27/34* (2013.01); *A61L 27/52* (2013.01); *A61L 27/54* (2013.01); *A61L 29/06* (2013.01); *A61L 29/085* (2013.01); *A61L 29/145* (2013.01); *A61L 29/16* (2013.01); *A61L 31/10* (2013.01); *A61L 31/16* (2013.01); *C08G 77/20* (2013.01); *G02B 1/043* (2013.01); *G02C 7/049* (2013.01); *A61F 2/14* (2013.01); *A61F 2250/0067* (2013.01); *A61L 2300/406* (2013.01); *A61L 2300/41* (2013.01); *A61L 2300/428* (2013.01); *A61L 2400/12* (2013.01); *A61L 2400/18* (2013.01); *A61L 2430/16* (2013.01); *C08G 2210/00* (2013.01)

(58) Field of Classification Search
CPC ........ A61L 31/145; A61L 15/24; A61L 15/44; A61L 27/18; A61L 27/34; A61L 27/52; A61L 27/54; A61L 29/06; A61L 29/085; A61L 29/145; A61L 29/16; A61L 31/10; A61L 31/16; A61L 15/26; A61L 2300/406; A61L 2300/41; A61L 2300/428; A61L 2400/12; A61L 2400/18; A61L 2430/16; A61F 2/14; A61F 2250/0067; C08G 2210/00; C08G 77/20; G02B 1/043; G02C 7/049

See application file for complete search history.

(56) References Cited

U.S. PATENT DOCUMENTS

| | | |
|---|---|---|
| 4,168,112 A | 9/1979 | Ellis et al. |
| 4,321,261 A | 5/1982 | Ellis et al. |

(Continued)

FOREIGN PATENT DOCUMENTS

| | | |
|---|---|---|
| CN | 101932624 A | 12/2010 |
| EP | 3 395 376 A1 | 10/2018 |

(Continued)

OTHER PUBLICATIONS

Machine English translation of JP 2006-327949, Takeda et al., Dec. 7, 2006.*
Machine English translation of WO 2017/146102, Kitagawa, Aug. 31, 2017.*
International Search Report, issued in PCT/JP2019/047628, PCT/ISA/210, dated Feb. 10, 2020.

(Continued)

*Primary Examiner* — Patrick D Niland
(74) *Attorney, Agent, or Firm* — Birch, Stewart, Kolasch & Birch, LLP

(57) ABSTRACT

A medical device including a substrate and a hydrophilic polymer layer and satisfying the following conditions: (1) that the hydrophilic polymer layer is on at least a part of the substrate; (2) that the hydrophilic polymer layer contains: a hydrophilic polymer having an acidic group; and a compound having an acidic group and a ring structure; and (3) that a time during which a liquid film is retained on the surface of the medical device (a liquid film retention time) is 10 seconds or more after the medical device is stationarily immersed in a phosphate buffer solution, pulled up from the phosphate buffer solution, and retained in the air. The present invention provides a medical device in which a surface of a substrate is hydrophilized, and a method for manufacturing same by a simple method.

7 Claims, No Drawings

(51) Int. Cl.
*G02B 1/04* (2006.01)
*G02C 7/04* (2006.01)

(56) References Cited

U.S. PATENT DOCUMENTS

| | | | |
|---|---|---|---|
| 6,428,839 | B1 | 8/2002 | Künzler et al. |
| 2002/0006521 | A1 | 1/2002 | Shimoyama et al. |
| 2008/0100796 | A1 | 5/2008 | Pruitt et al. |
| 2009/0142321 | A1* | 6/2009 | Matsui ............... A61K 31/4415 424/94.1 |
| 2012/0026458 | A1 | 2/2012 | Qiu et al. |
| 2013/0118127 | A1 | 5/2013 | Kolluru et al. |
| 2014/0198294 | A1 | 7/2014 | Nakamura et al. |
| 2015/0027625 | A1 | 1/2015 | Wright et al. |
| 2019/0022282 | A1 | 1/2019 | Kitagawa et al. |
| 2020/0063065 | A1 | 2/2020 | Iso et al. |
| 2020/0139653 | A1 | 5/2020 | Kitagawa et al. |
| 2020/0215226 | A1 | 7/2020 | Kitagawa et al. |

FOREIGN PATENT DOCUMENTS

| | | |
|---|---|---|
| JP | 54-116947 A | 9/1979 |
| JP | 63-246718 A | 10/1988 |
| JP | 10-85320 A | 4/1998 |
| JP | 2002-47365 A | 2/2002 |
| JP | 2003-171686 A | 6/2003 |
| JP | 2003-535626 A | 12/2003 |
| JP | 2006327949 A * | 12/2006 |
| JP | 2010-508563 A | 3/2010 |
| JP | 2013-533517 A | 8/2013 |
| JP | 2014-533381 A | 12/2014 |
| JP | 2017-23374 A | 2/2017 |
| WO | WO 2013/024799 A1 | 2/2013 |
| WO | WO 2015/119256 A1 | 8/2015 |
| WO | WO 2017/146102 A1 | 8/2017 |
| WO | WO 2018/207644 A1 | 11/2018 |
| WO | WO 2019/031477 A1 | 2/2019 |

OTHER PUBLICATIONS

Written Opinion of the International Searching Authority, issued in PCT/JP2019/047628, PCT/ISA/237, dated Feb. 10, 2020.
Extended European Search Report for European Application No. 19896396.9, dated Jun. 2, 2022.

* cited by examiner

MEDICAL DEVICE AND METHOD OF MANUFACTURING SAME

TECHNICAL FIELD

The present invention relates to a medical device and a method for manufacturing the same.

BACKGROUND ART

There have hitherto been used devices using soft materials made of resins such as a silicone rubber and hydrogel and devices using hard materials such as metal and glass in various fields. Applications of devices using soft materials include medical devices for introduction into a living body and for covering a surface of a living body, biotechnology devices such as cell culture sheets and scaffold materials for tissue regeneration, and cosmetic devices such as facial packs. Applications of devices using hard materials include electric appliances such as personal computers, mobile phones, and displays; diagnostic and analysis tools such as ampules for use in injections, capillaries, and biosensing chips.

When various devices are introduced into a living body as a medical device or attached to a surface of a living body, it becomes important to perform surface modification of the medical device. If it is possible to impart better properties such as hydrophilicity, lubricity, biocompatibility, and medicinal effect than before surface modification to the medical device by surface modification, users (patients, etc.) can expect an improvement in tactile sensation, reduction of discomfort, a symptomatic improvement, and the like.

Various methods have been known as methods for modification of a surface of a substrate of medical devices.

CITATION LIST

Patent Literature

In background art, since it was difficult to impart sufficient hydrophilicity in the case of one polymer material, there has been known a method of laminating by forming a layer of each of two or more polymer materials one by one through coating (see, for example, Patent Literature 1). Of these, a method of laminating by forming a layer of each of two or more polymer materials one by one on a layer having a charge opposite to that of the lower layer to coat layers having alternately different charges is called a layer by layer method (LbL method) or the like. In such coating obtained by the LbL method, it is considered that each layer of a substrate and a polymer material is bonded to other layer by the electrostatic interaction.

There has also been known a method in which two or more polymer materials are crosslinked to a substrate and a polymer layer having a thickness of 0.1 μm or more is coated on the substrate (see, for example, Patent Literature 2).

To improve cost efficiency, there has recently been disclosed, as an improved method of the LbL method, a method in which a polyionic substance and a hydrolysate substance during autoclaving are used and the polyionic substance is adsorbed onto a surface of a silicone hydrogel by a single heat treatment and, at the same time, the surface of the silicone hydrogel is hydrophilized (see Patent Literature 3).

There is also disclosed a method in which two hydrophilic polymers are crosslinked on a surface of a silicone hydrogel by a single heat treatment (see Patent Literature 4).

There is also disclosed a surface coating of a contact lens with an ionic polymer (see Patent Literatures 5 to 7).

There is also disclosed surface coating of a medical device, which improves the wettability using a wetting agent without adding a coupling agent (see Patent Literature 8).

Patent Literature 1: WO 2013/024799 A
Patent Literature 2: JP 2013-533517 W
Patent Literature 3: JP 2010-508563 W
Patent Literature 4: JP 2014-533381 W
Patent Literature 5: JP 54-116947 A
Patent Literature 6: JP 63-246718 A
Patent Literature 7: JP 2002-047365 A
Patent Literature 8: JP 2003-535626 W

SUMMARY OF INVENTION

Technical Problem

However, in conventional LbL coating as mentioned in Patent Literature 1, it is usually performed to laminate multilayers of about 3 to 20 layers. Laminating multilayers increases the number of manufacturing processes, and thus, manufacturing costs may increase. As a result of a study on an LbL coating obtained by this method, a problem was found in durability.

In the coating using crosslinking as mentioned in Patent Literature 2, since a crosslinked polymer layer has a thickness of 0.1 μm or more, for example, in the case of using for a medical device such as an ophthalmic lens, if the lens is not strictly controlled, there is a problem that light refraction for focusing on the retina is easily disturbed thus causing poor visibility. Since there is a need to strictly control the thickness of the polymer layer and there is a need for a complicated process for crosslinking the polymer to the substrate, manufacturing costs may increase.

In the improved LbL coating as mentioned in Patent Literature 3, applicable substrate is limited to a hydrous hydrogel. As a result of further study on an LbL coating obtained by this method, performances such as surface hydrophilicity were insufficient.

With respect to the method in which two hydrophilic polymers are crosslinked on the surface of a silicone hydrogel by a single heat treatment as mentioned in Patent Literature 4, applicable substrate is also limited to a hydrous hydrogel. In addition, the heat treatment is carried out at a temperature of 115° C. to 125° C., and thus necessitates autoclaving. In the method as mentioned in Patent Literature 4, there is a need for a process in which a carboxyl group-containing polymer is crosslinked to a silicone hydrogel surface before a heat treatment. Via a covalent bond between an epoxide group of a crosslinkable hydrophilic polymer material and a carboxyl group crosslinked on the silicone hydrogel surface, a hydrophilic polymer is crosslinked on a lens surface. This crosslinking is performed in an aqueous solution. Since there is a need for such a complicated process, manufacturing costs may increase.

In surface coating of a contact lens with an ionic polymer as mentioned in Patent Literatures 5 to 7, performances such as surface hydrophilicity were still insufficient.

In surface coating of a medical device as mentioned in Patent Literature 8, performances such as surface hydrophilicity were still insufficient.

The present invention has been made in view of the aforementioned problems of background art. Thus, it is an object of the present invention to provide a medical device whose surface is hydrophilized, excellent in durability and a method for simply producing the same.

Solution to Problem

To achieve the above object, the present invention has the following structures.

The present invention relates to a medical device including a substrate and a hydrophilic polymer layer and satisfying the following conditions:
(1) that the hydrophilic polymer layer is on at least a part of the substrate;
(2) that the hydrophilic polymer layer contains: a hydrophilic polymer having an acidic group; and a compound having an acidic group and a ring structure; and
(3) that a time during which a liquid film is retained on the surface of the medical device (a liquid film retention time) is 10 seconds or more after the medical device is stationarily immersed in a phosphate buffer solution, pulled up from the phosphate buffer solution, and retained in the air.

The present invention is also directed to a method for manufacturing a medical device including a substrate and a hydrophilic polymer layer, the method including the steps of: disposing the substrate in a solution having an initial pH of 2.0 or higher and 6.0 or lower; and heating the solution; wherein the solution contains: a hydrophilic polymer having an acidic group; and a compound having an acidic group and a ring structure.

Advantageous Effects of Invention

According to the present invention, unlike background art, it is possible to obtain a medical device imparted with hydrophilicity and having excellent durability. Applicable substrate is not limited to a hydrous hydrogel and a silicone hydrogel. Such a medical devices can be obtained using a simpler heat treatment process which necessitates no pressurization.

DESCRIPTION OF EMBODIMENTS

The medical device of the present invention includes a substrate and a hydrophilic polymer layer, and satisfies the following conditions:
(1) that the hydrophilic polymer layer is on at least a part of the substrate;
(2) that the hydrophilic polymer layer contains: a hydrophilic polymer having an acidic group; and a compound having an acidic group and a ring structure; and
(3) that a time during which a liquid film is retained on the surface of the medical device (a liquid film retention time) is 10 seconds or more after the medical device is stationarily immersed in a phosphate buffer solution, pulled up from the phosphate buffer solution, and retained in the air.

The medical device of the present invention may have a lens shape and is preferably an ophthalmic lens. Specific examples thereof include ophthalmic lenses such as contact lens, intraocular lens, artificial cornea, corneal inlay, corneal onlay, and eyeglass lens.

The medical device of the present invention may be in the form of a tube. Examples of a tubular device include an infusion tube, a gas delivery tube, a drainage tube, a blood circuit, a coating tube, a catheter, a stent, a sheath, a tube connector, an access port, and the like.

The medical device of the present invention may be in the form of a sheet or a film. Specific examples thereof include a dermal covering material, a wound dressing material, a skin protection material, a skin medicine carrier, a biosensor chip, an endoscopic dressing material, and the like.

The medical device of the present invention may have a storage container shape. Specific examples thereof include a medicine carrier, a cuff, a drainage bag, and the like.

An ophthalmic lens, especially a contact lens, is one of the most preferred embodiments of the present invention.

In the present invention, it is possible to use, as a substrate of the medical device, both a hydrous substrate and a non-hydrous substrate. Examples of the material of the hydrous substrate include a hydrogel and a silicone hydrogel. The silicone hydrogel is particularly preferable because of having flexibility which imparts excellent comfort, and high oxygen permeability. Examples of the non-hydrous substrate include a low water content soft material and a low water content hard material.

The present invention is also applicable to an ordinary hydrogel containing no silicone and a hydrogel containing silicone (hereinafter also referred to as silicone hydrogel) with respect to the material of the hydrous substrate. It is possible to use particularly suitably for the silicone hydrogel since surface physical properties can be significantly improved.

Hereinafter, United States Adopted Names (USAN) may be used to represent the material. In the USAN, there are cases where variations of the material are expressed by adding symbols such as A, B, and C at the end. However, in the present specification, all variations are encompassed when no symbol is added at the end. For example, when simply written as "ocufilcon", it expresses all variations of "ocufilcon A", "ocufilcon B", "ocufilcon C", "ocufilcon D", "ocufilcon E", "ocufilcon F", and the like.

For example, when a hydrogel is a contact lens, specific example of the hydrogel is preferably a hydrogel including one or more items selected from the group belonging to contact lens classification Group 1 to Group 4 defined by Food and Drug Administration (FDA). One or more items selected from the group belonging to Group 2 and Group 4 are more preferable, and one or more items selected from the group belonging to Group 4 are particularly preferable because of exhibiting satisfactory water wettability and antifouling properties.

Group 1 represents a nonionic hydrogel lens having a moisture content of less than 50% by mass. Specific examples thereof include tefilcon, tetrafilcon, helfilcon, mafilcon, polymacon, and hioxifilcon.

Group 2 represents a nonionic hydrogel lens having a moisture content of 50% by mass or more. Specific examples thereof include alfafilcon, omafilcon, hioxifilcon, nelfilcon, nesofilcon, hilafilcon, and acofilcon. Omafilcon, hioxifilcon, nelfilcon, and nesofilcon are more preferable, omafilcon and hioxifilcon are still more preferable, and omafilcon is particularly preferable because of exhibiting satisfactory water wettability and antifouling properties.

Group 3 represents an ionic hydrogel lens having a moisture content of less than 50% by mass. Specific examples thereof include deltafilcon, and the like.

Group 4 represents an ionic hydrogel lens having a moisture content of 50% by mass or more. Specific examples thereof include etafilcon, focofilcon, ocufilcon, phemfilcon, methafilcon, and vilfilcon. Etafilcon, focofilcon, ocufilcon, and phemfilcon are more preferable, etafilcon and ocufilcon are still more preferable, and etafilcon is particularly preferable because of exhibiting satisfactory water wettability and antifouling properties.

For example, when the medical device is a contact lens, specific example of the silicone hydrogel is preferably a silicone hydrogel selected from the group belonging to contact lens classification Group 5 defined by Food and Drug Administration (FDA).

The silicone hydrogel is preferably a polymer which has a silicon atom in the main chain and/or side chain and has hydrophilicity, and examples thereof include a copolymer of a monomer having a siloxane bond and a hydrophilic monomer.

Specific examples thereof include lotrafilcon, galyfilcon, narafilcon, senofilcon, comfilcon, enfilcon, balafilcon, efrofilcon, fanfilcon, somofilcon, samfilcon, olifilcon, asmofilcon, formofilcon, stenfilcon, abafilcon, mangofilcon, riofilcon, sifilcon, larafilcon, and delefilcon. Lotrafilcon, galyfilcon, narafilcon, senofilcon, comfilcon, enfilcon, stenfilcon, somofilcon, delefilcon, balafilcon, and samfilcon are more preferable, lotrafilcon, narafilcon, senofilcon, comfilcon, and enfilcon are still more preferable, and narafilcon, senofilcon, and comfilcon are particularly preferable because of exhibiting satisfactory water wettability and lubricity.

The low water content soft material and the low water content hard material are preferably a material having a silicon atom because of exhibiting high oxygen permeability capable of supplying sufficient oxygen to the cornea in the case of using, for example, for a medical device such as an ophthalmic lens.

For example, when a low water content hard material is a contact lens, specific example of the low water content hard material is preferably a low water content hard material selected from the group belonging to contact lens classification defined by Food and Drug Administration (FDA).

The low water content hard material is preferably a polymer having a silicon atom in the main chain and/or side chain. Among the polymers having a silicon atom, those in which the silicon atom is contained in the polymer by a siloxane bond are preferable from the viewpoint of the oxygen permeability. Specific examples of the polymer include tris(trimethylsilyloxy)silyl]propyl methacrylate, polydimethylsiloxane having a double bond at both ends, a homopolymer using silicone-containing (meth)acrylate, or a copolymer of these monomers and other monomers.

Specific examples thereof include neofocon, pasifocon, telefocon, silafocon, paflufocon, petrafocon, fluorofocon, and tisilfocon. Neofocon, pasifocon, telefocon, silafocon, and tisilfocon are more preferable, neofocon, pasifocon, telefocon, and tisilfocon are still more preferable, and neofocon and tisilfocon are particularly preferable because of exhibiting satisfactory water wettability and antifouling properties.

When the medical device of the present invention is an embodiment other than the contact lens, examples of those suitable as the low water content hard material include polyethylene, polypropylene, polysulfone, polyetherimide, polystyrene, polymethyl methacrylate, polyamide, polyester, epoxy resin, polyurethane, polyvinyl chloride, and the like. Polysulfone, polystyrene, and polymethyl methacrylate are still more preferable, and polymethyl methacrylate is particularly preferable because of exhibiting satisfactory water wettability and antifouling properties.

Specific examples of the low water content soft material include low water content soft materials used in medical devices as mentioned in WO 2013/024799 A in which a moisture content is 10% by mass or less, an elastic modulus is 100 kPa or more and 2,000 kPa or less, and a tensile elongation is 50% or more and 3,000% or less. Elastofilcon is also suitable.

When the medical device of the present invention is an embodiment other than an ophthalmic lens, suitable examples of the low water content soft material include silicone elastomer, soft polyurethane, polyvinyl acetate, ethylene-vinyl acetate copolymer, soft polyester resin, soft acrylic resin, soft polyvinyl chloride, natural rubber, various synthetic rubbers, and the like.

According to the present invention, it is possible to impart moderate hydrophilicity and lubricity to a surface of the medical device even if the substrate may be hydrous or low hydrous. Therefore, the moisture content of substrate may be 0 to 99% by mass. The moisture content of the substrate is preferably 0.0001% by mass or more, and particularly preferably 0.001% by mass or more, since the effect of imparting moderate hydrophilicity and lubricity to the surface of the medical device is further enhanced. The moisture content of the substrate is preferably 60% by mass or less, more preferably 50% by mass or less, and still more preferably 40% by mass or less.

When the medical device is a contact lens, since it is easy to ensure the movement of the lens in eyes, the moisture content of the substrate is preferably 15% by mass or more, and sill more preferably 20% by mass or more.

The medical device of the present invention includes a hydrophilic polymer layer provided on at least a part of the substrate, and the hydrophilic polymer layer contains: a hydrophilic polymer having an acidic group; and a compound having an acidic group and a ring structure.

Here, the hydrophilic polymer layer is provided on at least a part of the substrate. The hydrophilic polymer layer may exist either on the surface of the substrate or inside the substrate. In addition, the hydrophilic polymer layers may exist both on the surface of the substrate and inside the substrate. To suitably express the hydrophilicity of the hydrophilic polymer, the hydrophilic polymer layer is provided preferably on at least a part of the surface of the substrate. Including a hydrophilic polymer layer provided on at least a part of the surface of the substrate enables hydrophilicity to be imparted to at least a part of the surface of the medical device. Alternatively, a part of the hydrophilic polymer layer formed on the surface may enter into the inside of the substrate.

In the medical device of the present invention, the material constituting the hydrophilic polymer layer is usually a material different from that of the substrate. However, as long as a predetermined effect can be obtained, the material constituting the hydrophilic polymer layer may be the same as the material constituting the substrate.

The hydrophilic polymer layer in the medical device of the present invention contains a hydrophilic polymer having an acidic group.

As used herein, a hydrophilic polymer refers to a polymer soluble in 100 parts by mass of water at room temperature (20 to 23° C.) in an amount of 0.0001 part by mass or more. The hydrophilic polymer is soluble in 100 parts by mass of water more preferably in an amount of 0.01 part by mass or more, still more preferably 0.1 part by mass or more, and particularly preferably 1 part by mass or more.

The hydrophilic polymer having an acidic group is preferable because it can form a surface excellent in not only water wettability but also antifouling properties against body fluid, and the like. The acidic group as used herein is preferably a group selected from a carboxy group and a sulfonic group, and particularly preferably a carboxy group. The acidic group may be in the form of a salt.

Examples of the hydrophilic polymer having an acidic group include polymethacrylic acid, polyacrylic acid, poly (vinylbenzoic acid), poly(thiophene-3-acetic acid), poly(4-styrenesulfonic acid), polyvinylsulfonic acid, poly(2-acrylamido-2-methylpropanesulfonic acid), and salts thereof. Those mentioned above are examples of a homopolymer, and it is also possible to suitably use a copolymer of hydrophilic monomers constituting the hydrophilic polymer, or a copolymer of the hydrophilic monomer and the other monomer.

When the hydrophilic polymer having an acidic group is a copolymer, the hydrophilic monomer having an acidic group and constituting the copolymer is preferably a monomer having a group selected from an allyl group, a vinyl group, and a (meth)acryloyl group in view of high polymerizability, and particularly preferably a monomer having a (meth)acryloyl group. Suitable examples of such monomer include (meth)acrylic acid, vinylbenzoic acid, styrenesulfonic acid, vinylsulfonic acid, 2-acrylamido-2-methylpropanesulfonic acid, and salts thereof. Of these, a monomer selected from (meth)acrylic acid, 2-acrylamido-2-methylpropanesulfonic acid, and salts thereof is more preferable, and a monomer selected from (meth)acrylic acid and salts thereof is particularly preferable.

It is preferable that the hydrophilic polymer having an acidic group has an amide group, in addition to the acidic group. When having an amide group, in addition to the acidic group, moderate viscosity is exhibited when the hydrophilic polymer is dissolved in water, thus making it possible that a surface having not only water wettability but also lubricity is formed on a substrate. An amide group in the present invention means a group having a structure represented by N—C=O.

Examples of the hydrophilic polymer having an acidic group and an amide group include polyamides having a carboxyl group, a copolymer of the hydrophilic monomer having an acidic group and a monomer having an amide group, and the like.

Suitable examples of the polyamides having a carboxyl group include polyamino acids such as polyaspartic acid and polyglutamic acid, and polypeptides.

In view of ease of polymerization, the monomer having an amide group is preferably a monomer selected from a monomer having a (meth)acrylamide group and N-vinylcarboxylic acid amide (including cyclic one). Suitable Examples of such a monomer include N-vinylpyrrolidone, N-vinylcaprolactam, N-vinylacetamide, N-methyl-N-vinylacetamide, N-vinylformamide, N,N-dimethylacrylamide, N,N-diethylacrylamide, N-isopropylacrylamide, N-methylacrylamide, N-ethylacrylamide, N-butylacrylamide, N-tert-butylacrylamide, N-hydroxymethylacrylamide, N-methoxymethylacrylamide, N-ethoxymethylacrylamide, N-propoxymethylacrylamide, N-isopropoxymethylacrylamide, N-(2-hydroxyethyl)acrylamide, N-butoxymethylacrylamide, N-isobutoxymethylacrylamide, N-hydroxymethylmethacrylamide, N-methoxymethylmethacrylamide, N-ethoxymethylmethacrylamide, N-propoxymethylmethacrylamide, N-butoxymethylmethacrylamide, N-isobutoxymethylmethacrylamide, acryloyl morpholine, and acrylamide. Of these, N-vinylpyrrolidone, N,N-dimethylacrylamide, and N,N-diethylacrylamide are preferable in view of the lubricity, and N,N-dimethylacrylamide is particularly preferable.

Preferred specific examples of the copolymer of a hydrophilic monomer having an acidic group and a monomer having an amide group include a (meth)acrylic acid/N-vinylpyrrolidone copolymer, a (meth)acrylic acid/N,N-dimethylacrylamide copolymer, a (meth)acrylic acid/N,N-diethylacrylamide copolymer, a 2-acrylamide-2-methylpropanesulfonic acid/N-vinylpyrrolidone copolymer, a 2-acrylamide-2-methylpropanesulfonic acid/N,N-dimethylacrylamide copolymer, and a 2-acrylamide-2-methylpropanesulfonic acid/N,N-diethylacrylamide copolymer. A (meth)acrylic acid/N,N-dimethylacrylamide copolymer is particularly preferable.

When using a copolymer of a hydrophilic monomer having an acidic group and a monomer having an amide group, the copolymerization ratio thereof is preferably in a range of 1/99 to 99/1 in terms of [mass of hydrophilic monomer having an acidic group]/[mass of monomer having an amide group]. The copolymerization ratio of the hydrophilic monomer having an acidic group is more preferably 2% by mass or more, still more preferably 5% by mass or more, yet more preferably 7% by mass or more, and even more preferably 10% by mass or more. The copolymerization ratio of the hydrophilic monomer having an acidic group is more preferably 90% by mass or less, still more preferably 80% by mass or less, and yet more preferably 70% by mass or less. The copolymerization ratio of the monomer having an amide group is more preferably 10% by mass or more, still more preferably 20% by mass or more, and yet more preferably 30% by mass or more. The copolymerization ratio of the monomer having an amide group is more preferably 98% by mass or less, still more preferably 95% by mass or less, yet more preferably 93% by mass or less, and even more preferably 90% by mass or less. When the copolymerization ratios of the hydrophilic monomer having an acidic group and the monomer having an amide group are in the above range, it becomes easy to develop functions such as lubricity and antifouling properties against body fluid.

In addition, the hydrophilic monomer having an acidic group and the monomer having an amide group can each be composed of two or more monomers that are copolymerized. In addition, one or more monomers having neither acidic group nor amide group can be copolymerized.

Suitable examples of the monomer other than the above monomers include hydroxyethyl (meth)acrylate, hydroxypropyl (meth)acrylate, hydroxybutyl (meth)acrylate, glycerol (meth)acrylate, caprolactone-modified 2-hydroxyethyl (meth)acrylate, N-(4-hydroxyphenyl)maleimide, hydroxystyrene, and vinyl alcohol (or carboxylic acid vinyl ester as a precursor). Of these, in view of ease of polymerization, a monomer having a (meth)acryloyl group is preferable and a (meth)acrylic acid ester monomer is more preferable. Of these, in view of improving antifouling properties against body fluid, hydroxyethyl (meth)acrylate, hydroxypropyl (meth)acrylate, and glycerol (meth)acrylate are preferable, and hydroxyethyl (meth)acrylate is particularly preferable. It is also possible to use a monomer having functions such as hydrophilicity, antibacterial properties, antifouling properties, and medicinal effects.

When a copolymer of a hydrophilic monomer having an acidic group and a monomer having an amide group is copolymerized with a third monomer component which is the monomer having neither acidic group nor amide group, the copolymerization ratio of the third monomer component is more preferably 2% by mass or more, still more preferably 5% by mass or more, and yet more preferably 10% by mass or more. The copolymerization ratio of the third monomer component is more preferably 90% by mass or less, still more preferably 80% by mass or less, and yet more preferably 70% by mass or less.

If the copolymerization ratios of the monomer having an acidic group, the monomer having an amide group, and the third monomer component are in the above range, functions such as lubricity and antifouling properties against body fluid are easily developed.

In addition to the hydrophilic polymer having an acidic group, one or more other hydrophilic polymers may be included in the hydrophilic polymer layer. Since the manufacturing method may be complicated, it is preferable that the hydrophilic polymer layer is made of only one hydrophilic polymer having an acidic group.

Here, one polymer means a polymer or a polymer group (isomers, complexes, etc.) produced by one synthesis reaction. When a copolymerized polymer is obtained by using plural monomers, even though the constituent monomer species are the same, a polymer synthesized by changing a compounding ratio is not said to be the same one kind of polymer.

The expression that the hydrophilic polymer layer is made of only one hydrophilic polymer having an acidic group means that the hydrophilic polymer layer does not contain any polymer other than the hydrophilic polymer having an acidic group, or even if it contains the other polymer, it means that the content of the other polymer is 3 parts by mass or less based on 100 parts by mass of the hydrophilic polymer having an acidic group. The content of the other polymer is more preferably 0.1 part by mass or less, and still more preferably 0.0001 part by mass or less.

Even if the other polymer is a basic polymer having a basic group, when the content is in the above range, it is possible to suppress the occurrence of a problem with transparency. Here, the basic group represents a basic functional group, and examples thereof include an amino group and a salt thereof. In background art, an acidic polymer and a basic polymer were used in combination to laminate a hydrophilic polymer on a surface of the substrate utilizing the electrostatic adsorption effect. However, according to the present invention, a hydrophilic polymer layer made of only one polymer can also be formed on a surface of the substrate.

When the hydrophilic polymer layer has a basic polymer, a number ratio of basic group/acidic group contained in the hydrophilic polymer layer is preferably 0.2 or less. Since a salt derived from a reaction between an acidic group and a basic group is not formed, and the hydrophilic polymer layer is excellent in transparency, the ratio is more preferably 0.1 or less, and still more preferably 0.05 or less.

The hydrophilic polymer having an acidic group constituting the hydrophilic polymer layer preferably forms one or more chemical bonds selected from a hydrogen bond, an ionic bond, a van der Waals bond, a hydrophobic bond, and complex formation with at least a part of the surface of the substrate. Here, the hydrophilic polymer layer may be bonded to the substrate through a covalent bond, or rather, the hydrophilic polymer layer preferably has no covalent bond with the substrate since it becomes possible to manufacture by a simple process.

The hydrophilic polymer layer in the medical device of the present invention contains not only a hydrophilic polymer having an acidic group but also a compound having an acidic group and a ring structure. Containing a compound having an acidic group and a ring structure makes it easier to form a hydrophilic polymer layer on a substrate under lower temperature heat treatment conditions or simpler heat treatment conditions necessitating no pressurization, and thus, is preferable.

Furthermore, the compound having an acidic group and a ring structure is preferably a compound having a medicinal effect(s) of one or more selected from the group consisting of an antibacterial agent, an antiallergic agent, a glaucoma therapeutic agent, an antiinflammatory agent, an anticataract agent, a cornea therapeutic agent, and a vitamin agent. Such a case makes it possible to impart a medicinal effect(s) to the above-mentioned hydrophilic polymer layer, and thus, is more preferable.

In the compound having an acidic group and a ring structure, the acidic group is preferably a group selected from a carboxy group, hydroxyl group, and sulfonic group, more preferably a carboxy group or hydroxyl group, still more preferably a carboxy group. It is most preferable that the compound has both a carboxyl group and a hydroxyl group. The acidic group may be in the form of a salt.

Example of the compound having an acidic group and a ring structure include dipotassium glycyrrhizinate, dipotassium glycyrrhizinate hydrate, pyridoxine hydrochloride, L-histidine, ibuprofen, indomethacin, etodolac, catechol, phenol, resorcinol, sodium benzoate, disodium phthalate, disodium terephthalate, and the like. Dipotassium glycyrrhizinate and dipotassium glycyrrhizinate hydrate are used as antiallergic agents. Pyridoxine hydrochloride and L-histidine are used as vitamin agents. Ibuprofen, indomethacin, and etodolac are used as antiinflammatory agents. Catechol, phenol, resorcinol, sodium benzoate, disodium phthalate, and disodium terephthalate are used as antibacterial agents or glaucoma therapeutic agents.

From the viewpoint of good solubility in a hydrophilic polymer solution and excellent handling properties, compounds preferable among others are compounds selected from dipotassium glycyrrhizinate, dipotassium glycyrrhizinate hydrate, pyridoxine hydrochloride, L-histidine, phenol, catechol, resorcinol, sodium benzoate, disodium phthalate, and disodium terephthalate. From the viewpoint of better easiness of forming a hydrophilic polymer layer on a substrate under more relaxed heat treatment conditions, more preferable compounds are compounds selected from dipotassium glycyrrhizinate, dipotassium glycyrrhizinate hydrate, pyridoxine hydrochloride, L-histidine, sodium benzoate, disodium phthalate, and disodium terephthalate. A still more preferable compound is dipotassium glycyrrhizinate or dipotassium glycyrrhizinate hydrate.

As long as the development of the hydrophilicity is not impaired, additives other than above-mentioned may be included in the hydrophilic polymer layer in the medical device of the present invention.

The medical device of the present invention includes a hydrophilic polymer layer provided on at least a part of a substrate. Including a hydrophilic polymer layer provided on at least a part of a substrate refers to, for example, having a polymer layer existing on the whole of a face of the substrate. In the case of a two-dimensional shape in which the substrate has no thickness or, if any, thickness can be neglected, the polymer layer preferably exists on the whole of one face of the substrate. Preferably, the polymer layer exists on the whole of all the faces of the substrate.

Since the hydrophilic polymer layer can be manufactured by a simple process regardless of whether the substrate is hydrous or non-hydrous, it is preferred that a covalent bond does not exist between the hydrophilic polymer and the substrate. The absence of a covalent bond is judged by having no chemically reactive group or no group generated by the reaction of a chemically reactive group. Specific examples of the chemically reactive group include, but are not limited to, an azetidinium group, an epoxy group, an isocyanate group, an aziridine group, an azlactone group, and combinations thereof.

The thickness of the hydrophilic polymer layer is preferably 1 nm or more and less than 100 nm when observing a vertical cross section of the device in a dry state using a scanning transmission electron microscope. When the thickness is in the above range, it becomes easy to exhibit functions such as water wettability and lubricity. The thickness is more preferably 5 nm or more, and still more preferably nm or more. The thickness is more preferably 95 nm or less, still more preferably 90 nm or less, still more preferably 85 nm or less, still more preferably 50 nm or less, still more preferably 30 nm or less, still more preferably 20 nm or less, still more preferably 15 nm or less, and particularly preferably 10 nm or less. When the thickness of the hydrophilic polymer layer is less than 100 nm, the hydrophilic polymer layer is excellent in water wettability and lubricity and, for example, in the case of using for a medical device such as an ophthalmic lens, refraction of light for focusing on the retina is not disturbed and poor visibility becomes hardly occurs.

In the medical device of the present invention, at least a part of the hydrophilic polymer layer preferably exists in a state of being mixed with the substrate. The state where the hydrophilic polymer layer is mixed with the substrate is determined by the fact that elements derived from the substrate are detected in at least a part of the cross-sectional structure of the substrate before and after the formation of the hydrophilic polymer layer and the hydrophilic polymer layer when a cross section of the medical device is observed using observation means capable of performing elemental analysis or composition analysis, such as scanning transmission electron microscopy, electron energy-loss spectroscopy, energy dispersive X-ray spectroscopy, or time-of-flight secondary ion mass spectrometry. By mixing the hydrophilic polymer layer with the substrate, the hydrophilic polymer layer can be firmly fixed to the substrate.

When at least a part of the hydrophilic polymer layer exists in a state of being mixed with the substrate, it is preferred to observe a two-layer structure of a "layer in which at least a part of a hydrophilic polymer layer is mixed with a substrate" (hereinafter referred to as a "mixed layer") and a "layer made of a hydrophilic polymer" (hereinafter referred to as a "single layer"). The thickness of the mixed layer is preferably 3% or more, more preferably 5% or more, and still more preferably 10% or more, based on the total thickness of the mixed layer and the single layer. The thickness of the mixed layer is preferably 98% or less, more preferably 95% or less, still more preferably 90% or less, and particularly preferably 80% or less, based on the total thickness of the mixed layer and the single layer. The ratio of 3% or more as the thickness ratio of the mixed layer leads to sufficient mixing of the hydrophilic polymer with the substrate, enabling the hydrophilic polymer to be more firmly fixed on the substrate, and thus, is preferable. In addition, 98% or less of the thickness ratio of the mixed layer more easily causes the hydrophilicity of the hydrophilic polymer to be developed sufficiently, and thus, is preferable.

When the medical device of the present invention is, for example, a medical device which is used by being attached to a surface of a living body or an ophthalmic device such as an ophthalmic lens, the liquid film retention time on the surface of the medical device is preferably long from the viewpoint of preventing from sticking to the skin of users and preventing from sticking to the cornea of wearers.

A liquid film retention time in the present invention refers to a time during which a liquid film is retained on the surface of the medical device of the present invention after the medical device is stationarily immersed in a phosphate buffer solution, pulled up from the phosphate buffer solution, and retained in the air. Specifically, when the medical device stationarily immersed in a phosphate buffer solution is pulled up from the solution and retained so that the surface of the medical device can be vertical in the air, the liquid film retention time is from the point of time when the medical device starts being retained so as to be vertical to the point of time when the liquid film of the phosphate buffer solution covering the surface of the device is broken. The expression "the liquid film is broken" means a state where a phenomenon of repelling water on the surface of the medical device occurs, and where the surface of the medical device becomes no longer covered wholly with the liquid film.

For the medical device of the present invention, a time during which a liquid film is retained on the surface of the device (a liquid film retention time) is 10 seconds or more after the device is stationarily immersed in a phosphate buffer solution, pulled up from the phosphate buffer solution, and retained in the air. In addition, the liquid film retention time is preferably 15 seconds or more, more preferably 20 seconds or more. The upper limit of the liquid film retention time is not limited to any particular range, and is preferably 300 seconds or less, more preferably 200 seconds or less, because the medical device of the present invention involves causing moisture to be more easily evaporated from the surface of the medical device, thus causing the effect of the hydrophilic polymer layer to be low, when the liquid film retention time is too long.

When the medical device of the present invention is an ophthalmic device such as an ophthalmic lens, the dynamic contact angle of the surface of the medical device is preferably low from the viewpoint of preventing from sticking to the cornea of wearers. The dynamic contact angle is preferably 60° or less, more preferably 55° or less, and particularly preferably 50° or less. The dynamic contact angle (during advancing, immersion rate: 0.1 mm/sec) is measured using a sample wetted with a phosphate buffer solution. Being wetted with a phosphate buffer solution refers to the state where a sample is immersed in a phosphate buffer solution and left to stand at room temperature for 24 hours or more.

When the medical device of the present invention is a medical device which is used by being inserted into a living body, a surface of the medical device preferably has excellent lubricity. An indicator representing the lubricity, the friction coefficient measured by the method mentioned in Examples of the present specification is preferably small. The friction coefficient is preferably 0.7 or less, more preferably 0.5 or less, and particularly preferably 0.3 or less. If the friction is extremely small, it may be difficult to handle during wearing, so that the friction coefficient is preferably 0.001 or more, and more preferably 0.002 or more.

The tensile elastic modulus of the medical device of the present invention should be appropriately selected according to the type of the medical device. In the case of a soft medical device such as an ophthalmic lens, the tensile elastic modulus is preferably 10 MPa or less, preferably 5 MPa or less, more preferably 3 MPa or less, still more preferably 2 MPa or less, yet more preferably 1 MPa or less, and most preferably 0.6 MPa or less. The tensile elastic modulus is preferably 0.01 MPa or more, more preferably 0.1 MPa or more, still more preferably 0.2 MPa or more, and most preferably 0.25 MPa or more. In the case of a soft medical device such as an ophthalmic lens, too small tensile elastic modulus may lead to difficulty in handling because of being excessive in softness. Too large tensile elastic modulus may lead to deterioration of comfort because of being excessive in hardness.

The antifouling properties of the medical device of the present invention can be evaluated by the deposition of lipid (methyl palmitate). The smaller the deposition amount by these evaluations, the more tactile sensation is excellent and bacterial propagation risk is reduced, favorably. Details of a method for measuring antifouling properties will be mentioned later.

Next, a method for manufacturing a medical device of the present invention will be described.

A method for manufacturing a medical device according to the present invention is a method for manufacturing a medical device including a substrate and a hydrophilic polymer layer, the method including the steps of: disposing the substrate in a solution having an initial pH of 2.0 or higher and 6.0 or lower; and heating the solution, wherein the solution contains: a hydrophilic polymer having an acidic group; and a compound having an acidic group and a ring structure. In addition, the solution may contain an acid.

Here, the inventors of the present invention have found that excellent water wettability and lubricity can be imparted to a medical device by an extremely simple method in which a substrate is heated in a state of being disposed in a solution having an initial pH of 2.0 or higher and 6.0 or lower, which contains: a hydrophilic polymer having an acidic group; and a compound having an acidic group and a ring structure. Furthermore, the conditions to be adopted for the heating can be based on a low temperature of less than 100° C., and thus, do not always necessitate pressurization.

According to this method, a substrate with a hydrophilic polymer layer having an acidic group layer can be obtained without using a conventionally known special method, for example, a method in which the electrostatic adsorption effect using an acidic polymer in combination with a basic polymer is utilized. Furthermore, in cases where the compound having an acidic group and a ring structure is a compound having a medicinal effect(s) of one or more selected from the group consisting of an antibacterial agent, an antiallergic agent, a glaucoma therapeutic agent, an antiinflammatory agent, an anticataract agent, a cornea therapeutic agent, and a vitamin agent, the hydrophilic polymer layer can be provided with the medicinal effect(s). This leads to an industrially very important meaning from the viewpoint of shortening the manufacturing process.

The hydrophilic polymer preferably has a molecular weight of 2,000 to 1,500,000. The molecular weight is preferably 50,000 or more, more preferably 250,000 or more, and still more preferably 500,000 or more, because of exhibiting sufficient water wettability and lubricity. The molecular weight is preferably 1,200,000 or less, more preferably 1,000,000 or less, and still more preferably 900,000 or less. Here, a mass average molecular weight in terms of polyethylene glycol measured by a gel permeation chromatography method (aqueous solvent) is used as the molecular weight.

An increase in concentration of the hydrophilic polymer in the solution during manufacture usually leads to an increase in thickness of the thus obtained hydrophilic polymer layer. However, too high concentration of the hydrophilic polymer may lead to an increase in difficulty of handling during manufacture due to an increase in viscosity, so that the concentration in the solution of the hydrophilic polymer is preferably 0.0001 to 30% by mass. The concentration of the hydrophilic polymer is more preferably 0.001% by mass or more, and still more preferably 0.005% by mass or more. The concentration of the hydrophilic polymer is more preferably 20% by mass or less, and still more preferably 15% by mass or less.

Furthermore, in cases where the concentration of the compound having an acidic group and a ring structure is too high in the solution during manufacture, the film thickness of the hydrophilic polymer layer is excessive and can lead to an increase in difficulty of handling during manufacture, and thus, the concentration of the compound having an acidic group and a ring structure is preferably 0.0001 to 0.4% by mass in the solution. The concentration of the compound having an acidic group and a ring structure is more preferably 0.001% by mass or more, and still more preferably 0.005% by mass or more. In addition, the concentration of the compound having an acidic group and a ring structure is more preferably 0.3% by mass or less, and still more preferably 0.2% by mass or less.

In the above process, the initial pH value of the solution containing a hydrophilic polymer is preferably in a range of 2.0 to 6.0 since turbidity does not occur in the solution to obtain a medical device having satisfactory transparency. The initial pH is more preferably 2.1 or higher, still more preferably 2.2 or higher, yet more preferably 2.4 or higher, and particularly preferably 2.5 or higher. The initial pH is more preferably 5.0 or lower, still more preferably 4.0 or lower, and yet more preferably less than 3.5.

If the initial pH is 2.0 or higher, turbidity of the solution is less likely to occur. It is preferred that turbidity does not occur in the solution because the surface of the medical device may have high water wettability and lubricity. When the initial pH is 6.0 or lower, the thus obtained hydrophilic polymer layer is more likely to exist in mixture with the substrate, causing no decrease in water wettability and lubricity of the surface of the medical device, and thus, is preferable.

Since it is possible to impart excellent water wettability and lubricity to the substrate, when the substrate is a material having a silicon atom, the initial pH of the solution containing a hydrophilic polymer is preferably in a range of 3.4 or lower, more preferably 3.3 or lower, and still more preferably 3.2 or lower. When the substrate is a material having no silicon atom, the initial pH is preferably in a range of 4.0 or lower, more preferably 3.5 or lower, and still more preferably 3.3 or lower.

The pH of the solution can be measured using a pH meter (e.g., pH meter Eutech pH 2700 (Eutech Instruments)). Here, the initial pH of the solution containing a hydrophilic polymer means the pH value of the solution measured after adding all of the hydrophilic polymer, the compound, and the acid to the solution, followed by stirring at room temperature (23 to 25° C.) for 2 hours with a rotor to thereby make the solution uniform, and before disposing a substrate in the solution and heating the substrate. In the present invention, the pH value is rounded off to one decimal place.

The pH of the solution can change when a heating operation is performed. The pH of the solution after the heating operation is preferably 2.0 to 6.0. The pH after heating is more preferably 2.1 or higher, still more preferably 2.2 or higher, and particularly preferably 2.3 or higher. The pH after heating is more preferably 5.9 or lower, still more preferably 5.5 or lower, yet more preferably 5.0 or lower, and particularly preferably 4.8 or lower. When the pH of the solution after the heating operation is in the above range, the pH of the solution is maintained at appropriate conditions during the heating process, thus obtaining suitable physical properties of the thus obtained medical device. After modifying the surface of the substrate used for the medical device by performing the heating operation in the present invention, the pH can be adjusted by performing a neutralization treatment or adding water. Here, the pH of the solution after the heating operation is a pH exhibited before such a pH adjustment treatment is made.

Preferable examples of solvents for the solution containing a hydrophilic polymer include water-soluble organic solvents, water, and solvent mixtures thereof. Water and mixtures of water and a water-soluble organic solvent are more preferable, and water is most preferable. Suitable water-soluble organic solvents are various water-soluble alcohols, water-soluble alcohols having 6 or less carbon atoms are more suitable, and water-soluble alcohols having 5 or less carbon atoms are still more suitable.

The pH of the solution can be adjusted by adding an acid to the solution. Such an acid is preferably a low-molecular-weight acid having no ring structure. Here, a low molecular weight means that the molecular weight is 500 or less, preferably 300 or less, still more preferably 250 or less. Examples of usable low-molecular-weight acids having no ring structure include organic acids and inorganic acids. Preferred specific examples of the organic acid include acetic acid, citric acid, formic acid, ascorbic acid, trifluoromethanesulfonic acid, methanesulfonic acid, propionic acid, butyric acid, glycolic acid, lactic acid, malic acid, and the like. Preferred specific examples of the inorganic acid include nitric acid, sulfuric acid, phosphoric acid, hydrochloric acid, and the like. Of these, an organic acid is preferable, an organic acid having 1 to 20 carbon atoms is more preferable, and an organic acid having 2 to carbon atoms is still more preferable, from the viewpoint of the fact that it is easy to obtain more excellent hydrophilic surface, safety to a living body is high, and it is easy to handle. Of these organic acids, an acid(s) selected from acetic acid, citric acid, formic acid, ascorbic acid, trifluoromethanesulfonic acid, methanesulfonic acid, propionic acid, butyric acid, glycolic acid, lactic acid, and malic acid is/are preferable, an acid(s) selected from formic acid, malic acid, citric acid, and ascorbic acid is/are more preferable, and citric acid or ascorbic acid is still more preferable. Of these inorganic acids, sulfuric acid is preferable, from the viewpoint of low volatility, odorless, and easy to handle.

Since it becomes easy to finely adjust the pH, and the substrate is less likely to become turbid when the substrate is a material containing a hydrophobic component, a buffering agent is preferably added to the solution.

It is possible to use, as the buffering agent, a physiologically compatible known buffering agent. Examples are as follows: boric acid, borate (e.g., sodium borate), citric acid, citrates (e.g., potassium citrate), bicarbonate (e.g., sodium bicarbonate), phosphate buffer solution (e.g., $Na_2HPO_4$, $NaH_2PO_4$, and $KH_2PO_4$), TRIS (tris(hydroxymethyl)aminomethane), 2-bis(2-hydroxyethyl)amino-2-(hydroxymethyl)-1,3-propanediol, bis-aminopolyol, triethanolamine, ACES (N-(2-acetamide)-2-aminoethanesulfonic acid), BES (N,N-bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid)), TES (N-[tris(hydroxymethyl)methyl]-2-aminoethanesulfonic acid), and salts thereof.

The buffering agent is used in the effective amount required to achieve desired pH. Usually, the buffering agent exists in the solution in an amount of 0.001% by mass to 2% by mass, preferably 0.01% by mass to 1% by mass, and more preferably 0.05% by mass to 0.30% by mass. The amount may be in a range of a combination of either the upper limit or the lower limit.

Examples of the heating method in the heating operation include a temperature-raising method (with hot air), a high-pressure steam sterilization method, irradiation with electromagnetic waves (γ ray, microwave, etc.), a dry heat method, a flame method, and the like. From the viewpoint of the water wettability, lubricity, and shortening of the production process, a temperature-raising method (with hot air) is most preferable. A preferable device to be used is an automatic oven or an oven with internal hot air circulation.

The heating temperature is preferably in the range of from 50° C. to 100° C. from the viewpoint of obtaining a medical device surface exhibiting satisfactory water wettability and lubricity and exerting less influence on the strength of the medical device itself. The heating temperature is more preferably 55° C. or higher, still more preferably 60° C. or higher, yet more preferably 65° C. or higher, and particularly preferably 70° C. or higher. The heating temperature is more preferably 99° C. or lower, still more preferably 90° C. or lower, and particularly preferably 85° C. or lower.

A heating operation according to background art enables a hydrophilic polymer having a hydroxyl group to be more fixed on the surface of a substrate under conditions of 100° C. or more which necessitate pressurization (for example, WO2017/146102).

However, the present inventors have made a study, and succeeded in causing the treatment temperature to be lower, through the discovery that, even under low temperature conditions necessitating no pressurization, using both a compound having an acidic group and a ring structure and a hydrophilic polymer having an acidic group enables the hydrophilic polymer layer to be fixed on the surface of the device.

Although the reason for this is not clear, the present inventors infer that a compound having an acidic group and a ring structure facilitates intermolecular interaction such as hydrogen bonding between a hydrophilic polymer having an acidic group and a device, thus enabling the hydrophilic polymer layer to be fixed on the surface of the device even under low temperature conditions necessitating no pressurization.

In this regard, in cases where the compound having an acidic group and a ring structure remains in a medical device obtained by the manufacturing method according to the present invention, and in cases where the compound has the medicinal effects, the medicinal effects which the compound originally has can be advantageously imparted to the obtained medical device as above-mentioned. However, the manufacturing method according to the present invention makes it possible that the above-mentioned effect of causing the treatment temperature to be lower is enjoyed even in cases where the compound having an acidic group and a ring structure does not remain in the medical device.

If the heating time is too short, a medical device surface exhibiting satisfactory water wettability and lubricity is unlikely to be obtained. Meanwhile, if the heating time is too long, an adverse influence may be exerted on the strength of the medical device itself, the heating time is preferably 5 minutes to 600 minutes. The heating time is more preferably 10 minutes or more, and still more preferably 15 minutes or more. The heating time is more preferably 400 minutes or less, and still more preferably 300 minutes or less.

After the above heat treatment, the medical device thus obtained may be further subjected to the other treatment. Examples of the other treatment include methods such as a method in which a similar heat treatment is performed in a solution containing a hydrophilic polymer, a method in which a similar heat treatment is performed by using a solution containing no hydrophilic polymer in place of the solution, a method in which irradiation with radiation is performed, a method of performing a layer by layer treatment (LbL treatment) in coatings of polymer materials each having an opposite charge are alternately formed layer by layer, a method in which a crosslinking treatment with metal ions is performed, a method in which a chemical crosslinking treatment is performed, and the like.

Before the above heat treatment, the substrate may be subjected to a pretreatment. Examples of the pretreatment include a hydrolysis treatment with an acid such as polyacrylic acid, or an alkali such as sodium hydroxide. However, in light of the idea of the present invention which enables hydrophilization of a substrate surface by a simple method, a treatment is preferably performed as long as the manufacturing process does not become too complicated.

Radiations used for the above irradiation with radiation are preferably various ion beams, electron beams, positron beams, X-rays, γ rays, and neutron rays, more preferably electron beams or γ rays, and most preferably γ rays.

As the above LbL treatment, for example, a treatment using an acidic polymer and a basic polymer as mentioned in WO 2013/024800 A is preferably used.

Metal ions used for the above crosslinking treatment with metal ions are preferably various metal ions, more preferably monovalent and divalent metal ions, and most preferably divalent metal ions. Alternatively, a chelate complex may also be used.

As the above chemical crosslinking treatment, for example, a reaction between an epoxy group and a carboxyl group as mentioned in JP 2014-533381 A and a crosslinking treatment formed between known acidic hydrophilic polymers having a hydroxyl group may be used.

In the above method in which a similar heat treatment is performed by using a solution containing no hydrophilic polymer in place of the solution, the solution containing no hydrophilic polymer is not particularly limited and a buffering agent solution is preferable. The above-mentioned substances can be used as the buffering agent.

The pH of the buffering agent solution is preferably within a physiologically acceptable range of 6.3 to 7.8. The pH of the buffering agent solution is preferably 6.5 or higher, and still more preferably 6.8 or higher. The pH of the buffering agent solution is preferably 7.6 or lower, and more preferably 7.4 or lower.

In the manufacturing method of the present invention, the moisture content change rate between the medical device obtained after completion of the heating step and the substrate before starting the heating step is preferably 10 percentage points or less. Here, the moisture content change rate (percentage points) means a difference between the moisture content (% by mass) of the resulting medical device and the moisture content (% by mass) of the substrate as a raw material of the medical device.

The moisture content change rate of the medical device before and after formation of the hydrophilic polymer layer is preferably 10 percentage points or less, more preferably 8 percentage points or less, and particularly preferably 6 percentage points or less, from the viewpoint of preventing poor visibility or deformation caused by distortion of a refractive index due to an improvement in moisture content when the medical device is used in an ophthalmic device such as an ophthalmic lens. Details of the method of measuring the moisture content change rate will be mentioned later.

The tensile elastic modulus change rate before and after formation of the hydrophilic polymer layer of the medical device of the present invention is preferably 15% or less, more preferably 14% or less, and particularly preferably 13% or less. Too large tensile elastic modulus change rate may lead to deformation and poor tactile sensation, unfavorably. Details of the method of measuring the tensile elastic modulus change rate will be mentioned later.

The size change rate before and after formation of the hydrophilic polymer layer of the medical device is preferably 5% or less, more preferably 4 or less, and particularly preferably 3% or less, from the viewpoint of preventing corneal injury caused by deformation when used in an ophthalmic device such as an ophthalmic lens. Details of the method of measuring the size change rate will be mentioned later.

EXAMPLES

The present invention will be described more specifically by way of Examples, but the present invention is not limited to these Examples. First, analytical method and evaluation method will be shown.

<Water Wettability (Liquid Film Retention Time)>

A medical device was left to stand in a storage container at room temperature for 24 hours or more. In cases where a commercially available contact lens mentioned in Comparative Examples was itself evaluated, the medical device was lightly washed in 50 mL of a phosphate buffer solution in a beaker at room temperature and then left to stand in 50 mL of a fresh phosphate buffer solution for 24 hours or more.

From the phosphate buffer solution in which the medical device was stationarily immersed, the medical device was pulled up and retained in the air, and the time during which the liquid film was retained on the surface of the medical device was visually observed. Three measurements were taken of the liquid film retention time, and the average of the measurements was judged according to the following criteria. Here, the time during which the liquid film is retained is from the point of time when the medical device starts being retained so as to be vertical in the air to the point of time when the liquid film of the phosphate buffer solution covering the surface of the medical device is broken.

A: A liquid film on a surface is retained for 20 seconds or more.
B: A liquid film on a surface is broken after 15 seconds or more and less than 20 seconds.
C: A liquid film on a surface is broken after 10 seconds or more and less than 15 seconds.
D: A liquid film on a surface is broken after 1 second or more and less than 10 seconds.
E: A liquid film on a surface is instantly broken (less than 1 second).

<Lubricity>

The medical device manufactured in each Example was left to stand at room temperature for 24 hours or more in a storage container. In cases where a commercially available contact lens in Comparative Examples was itself evaluated, the medical device was lightly washed in 50 mL of a phosphate buffer solution in a beaker at room temperature and then left to stand in 50 mL of a fresh phosphate buffer solution for 24 hours or more.

The medical device was pulled up from the phosphate buffer solution in which the medical device was stationarily immersed, and subjected to sensory evaluation when rubbing with a human finger five times.

A: There is extremely excellent lubricity (the finger slides to flow on a medical device surface and feel no resistance).
B: There is lubricity intermediate between A and C.
C: There is moderate lubricity (the finger slides on a medical device surface and hardly feels resistance).
D: Almost no lubricity (intermediate between C and E).
E: No lubricity (the finger does not easily slide on a medical device surface and feel large resistance).

<Moisture Content of Substrate and Medical Device>

A substrate was immersed in a phosphate buffer solution and left to stand at room temperature for 24 hours or more. The substrate was pulled out from the phosphate buffer solution and, after wiping off the surface moisture with a wiping cloth ("Kimwipes" (registered trademark) manufactured by NIPPON PAPER CRECIA CO., LTD.), the mass (Ww) of the substrate was measured. Thereafter, the substrate was dried at 40° C. for 2 hours in a vacuum dryer and the mass (Wd) was measured. From these masses, the moisture content of the substrate was calculated in accordance with the following formula (1). The case where the obtained value was less than 1% was judged as below the measurement limit, and the column in the table was filled with "less than 1%". Three measurements were taken of the moisture content, and the average of the measurements was regarded as the moisture content. The moisture content of the substrate with a hydrophilic polymer layer, i.e., the medical device was also calculated in the same manner.

$$\text{Moisture content (\%) of substrate} = 100 \times (Ww - Wd)/Ww \quad \text{Formula (1)}$$

<Moisture Content Change Rate of Substrate Between Before and after Formation of Hydrophilic Polymer Layer>

From the measurement results of the moisture content of the substrate and the medical device, the moisture content change rate was calculated by the following formula (2).

$$\text{Moisture content change rate (percentage points) of Substrate before and after formation of hydrophilic polymer layer} = \text{moisture content (\% by mass) of medical device} - \text{moisture content (\% by mass) of substrate} \quad \text{Formula (2)}$$

<Friction Coefficient>

Under the following conditions, five measurements were taken of the friction coefficient of the medical device surface wetted with a phosphate buffer solution (preservation solution in a package in the case of measuring a commercially available contact lens), and the average of the measurements was regarded as the friction coefficient.

Apparatus: Friction tester KES-SE (manufactured by Kato Tech Co., Ltd.)
Friction SENS: H
Measurement SPEED: 2×1 mm/sec
Friction load: 44 g <Lipid Deposition Amount>

In a 20 cc screw tube, 0.03 g of methyl palmitate, 10 g of pure water, and 1 sample having a contact lens shape were placed. The screw tube was shaken for 3 hours under the conditions at 37° C. and 165 rpm. After shaking, the sample in the screw tube was scrubbed with tap water at 40° C. and a household liquid detergent ("Mama Lemon (registered trademark)" manufactured by Lion Corporation). The washed sample was placed in a screw tube containing a phosphate buffer solution and stored in a refrigerator at 4° C. for 1 hour. Thereafter, the sample was visually observed, and if the turbid portion exists, it was judged that methyl palmitate is deposited and the area of the portion in which methyl palmitate is deposited to the entire surface of the sample was observed.

<Tensile Elastic Modulus>

A test piece having a width (minimum part) of 5 mm and a length of 14 mm was cut out from a substrate having a contact lens shape using a prescribed punching die. Using the test piece, a tensile test was performed using Tensilon Model RTG-1210 manufactured by A&D Company, Limited. A pulling rate was 100 mm/min and a distance between grips (initial) was 5 mm. Measurements were taken of both a substrate before formation of a hydrophilic polymer layer and a medical device after formation of a hydrophilic polymer layer. Eight measurements were taken, and the average of the N=6 measurements excluding the maximum value and the minimum value was regarded as the tensile elastic modulus. The tensile elastic modulus of the substrate with a hydrophilic polymer layer, i.e., the medical device was also measured in the same manner.

<Tensile Elastic Modulus Change Rate of Substrate Before and After Formation of Hydrophilic Polymer Layer>

From the measurement results of the tensile elastic modulus of the substrate and the medical device, calculation was performed by the following formula (3).

$$\text{Tensile elastic modulus change rate (\%) of Substrate before and after formation of hydrophilic polymer layer} = (\text{tensile elastic modulus of medical device after formation of hydrophilic polymer layer} - \text{tensile elastic modulus of substrate before formation of hydrophilic polymer layer})/\text{tensile elastic modulus of substrate before formation of hydrophilic polymer layer} \times 100 \quad \text{Formula (3)}.$$

<Size>

Three measurements were taken of the diameter of a substrate having a contact lens shape, and the average of the measurements was regarded as the size. The size of the substrate with a hydrophilic polymer layer, i.e., the medical device was also measured in the same manner.

<Size Change Rate Before and After Formation of Hydrophilic Polymer Layer>

From the measurement results of the size of the substrate and the medical device, calculation was performed by the following formula (4).

$$\text{Size change rate (\%) before and after formation of hydrophilic polymer layer} = (\text{size of medical device after formation of hydrophilic polymer layer} - \text{size of substrate before formation of hydrophilic polymer layer})/\text{size of substrate before formation of hydrophilic polymer layer} \times 100 \quad \text{Formula (4)}$$

<Molecular Weight Measurement>

The molecular weight of a hydrophilic polymer was measured under the following conditions.

Apparatus: Prominence GPC system manufactured by Shimadzu Corporation
Pump: LC-20AD
Autosampler: SIL-20AHT
Column oven: CTO-20A
Detector: RID-10A
Column: GMPWXL manufactured by Tosoh Corporation (7.8 mm in inner diameter×30 cm, particle diameter of 13 μm)
Solvent: water/methanol=1/1 (0.1 N lithium nitrate is added)

Flow rate: 0.5 mL/minute
Measurement time: 30 minutes
Sample concentration: 0.1 to 0.3% by mass
Sample injection amount: 100 μL
Standard sample: Polyethylene oxide standard sample manufactured by Agilent Technologies, Inc. (0.1 kD to 1258 kD)

<pH Measurement Method>

The pH of the solution was measured using a pH meter Eutech pH 2700 (manufactured by Eutech Instruments Pte Ltd). In the table, the initial pH of a solution containing a hydrophilic polymer was determined by adding all of the hydrophilic polymer, the compound having an acidic group and a ring structure, and the acid to the solution mentioned in each Example, followed by stirring at room temperature (23 to 25° C.) for 2 hours with a rotor to thereby make the solution uniform. In the table, "pH after heat treatment" is the pH measured immediately after the solution was cooled to room temperature (23 to 25° C.) after a heat treatment was performed once.

<Elemental Composition Analysis of Hydrophilic Polymer Layer>

Elemental composition analysis of a hydrophilic polymer layer was performed by observing a cross section of a medical device in a dry state using energy dispersive X-ray spectroscopy.

<Apparatus: Field Emission Electron Microscope, JEM2100F, Manufactured by JEOL Ltd.>

EDX (Energy dispersive X-ray Spectroscopy)
JED-2300T (a Si(Li) semiconductor detector of a UTW type), manufactured by JEOL Ltd.

<System: Analysis Station>

Acceleration voltage: 200 kV
Beam diameter: 0.7 nm
Image acquisition: Digital Micrograph <Sample Preparation>

Sample was prepared by a method of staining ultrathin section with RuO4. When it is difficult to discriminate between a substrate and a coat layer, the sample may be stained with $OsO_4$.

<Thickness of Hydrophilic Polymer Layer>

The thickness of a hydrophilic polymer layer in a dry state was measured by observing a cross section of a medical device in a dry state using a transmission electron microscope.

Apparatus: Transmission electron microscope, Condition: Accelerating voltage of 100 kV
Sample preparation: Sample was prepared by a method of staining ultrathin section with $RuO_4$. When it is difficult to discriminate between a substrate and a hydrophilic polymer layer, the sample may be stained with $OsO_4$.

While changing three places, the thickness was measured at three places for each field of view, and an average of the thickness at nine places in total was mentioned.

Manufacturing Example 1

After preparing 28 parts by mass of a polydimethylsiloxane having a methacryloyl group at both ends represented by the formula (M1) (FM 7726, JNC Corporation, Mw: 30,000), 7 parts by mass of a silicone monomer represented by the formula (M2) (FM 0721, JNC Corporation, Mw: 5,000), 57.9 parts by mass of trifluoroethyl acrylate ("Viscoat" (registered trademark) 3F, Osaka Organic Chemical Industry Ltd.), 7 parts by mass of 2-ethylhexyl acrylate (Tokyo Chemical Industry Co., Ltd.), and 0.1 part by mass of dimethylaminoethyl acrylate (Kohjin Co., Ltd.), preparing 5,000 ppm of a photoinitiator "IRGACURE" (registered trademark) 819 (Nagase & Co., Ltd.), 5,000 ppm of a UV absorber (RUVA-93, Otsuka Chemical Co., Ltd.), and 100 ppm of a colorant (RB 246, Arran chemical) based on the total amount of these monomers, and preparing 10 parts by mass of t-amyl alcohol based on 100 parts by mass of the total amount of these monomers, all components were mixed, followed by stirring. The mixture thus obtained by stirring was filtered through a membrane filter (pore diameter: 0.45 μm) to remove insoluble substances to obtain a monomer mixture.

The above monomer mixture was poured into a contact lens mold made of a transparent resin (material on base curve side: polypropylene, material on front curve side: polypropylene) and then polymerized by irradiation with light (wavelength 405 nm (±5 nm), illuminance: 0 to 0.7 mW/cm², for 30 minutes) to obtain a molded body made of a low water content soft material having a silicon atom.

After the polymerization, the molded body thus obtained was immersed in an aqueous 100% by mass isopropyl alcohol solution at 60° C. for 1.5 hours together with the mold from which a front curve and a base curve were released, and then a molded body having a contact lens shape was removed from the mold. The molded body thus obtained was immersed in a large excess amount of an aqueous 100% by mass isopropyl alcohol solution maintained at 60° C. for 2 hours to extract impurities such as residual monomers. Thereafter, the molded body was dried at room temperature (23° C.) for 12 hours.

[Chemical Formula 1]

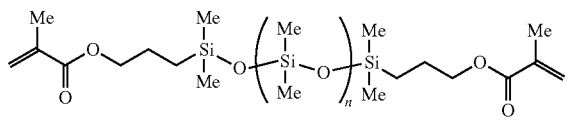

(M1)

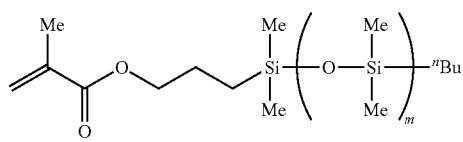

(M2)

<Phosphate Buffer Solution>

Each composition of the phosphate buffer solutions used in the processes of the following Examples and Comparative Examples and the above-mentioned measurements is as follows.

KCl: 0.2 g/L
$KH_2PO_4$: 0.2 g/L
NaCl: 8.0 g/L
$Na_2HPO_4$ (anhydrous): 1.15 g/L
EDTA: 0.25 g/L Example 1

A commercially available silicone hydrogel lens containing silicone as a main component "MyDay (registered trademark)" (stenfilcon A, manufactured by CooperVision Inc.) was used as a substrate. An aqueous solution containing 0.19% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.)

and 0.2% by mass of dipotassium glycyrrhizinate in a phosphate buffer solution was adjusted to pH 3.2 with citric acid. The substrate was immersed in the solution and heated at 80° C. for 30 minutes using the DKN602 Constant Temperature Oven (manufactured by Yamato Scientific Co., Ltd.). The medical device thus obtained was stationarily immersed in a phosphate buffer solution to be washed, and, after the phosphate buffer solution was replaced with a fresh phosphate buffer solution, the medical device was further heated in the autoclave at 121° C. for 30 minutes. The results of evaluating the obtained medical device using the above methods are shown in Tables 1 to 3.

Examples 2 to 7

An experiment was performed in the same manner as in Example 1 except that the compound having an acidic group and a ring structure was changed to a compound shown in Table 1. The results of evaluating the obtained medical device using the above methods are shown in Tables 1 to 3.

Example 8

An experiment was performed in the same manner as in Example 1 except that the conditions for heating in the solution containing a hydrophilic polymer having an acidic group and a compound having an acidic group and a ring structure were changed to the conditions for heating at 60° C. for 30 minutes. The results of evaluating the obtained medical device using the above methods are shown in Tables 1 to 3.

Example 9

An experiment was performed in the same manner as in Example 5 except that the initial pH of the solution containing a hydrophilic polymer having an acidic group and a compound having an acidic group and a ring structure was changed to 2.6. The results of evaluating the obtained medical device using the above methods are shown in Tables 1 to 3.

Example 10

A commercially available silicone hydrogel lens containing silicone as a main component "MyDay (registered trademark)" (stenfilcon A, manufactured by CooperVision Inc.) was used as a substrate. An aqueous solution containing 0.19% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) and 0.2% by mass of disodium terephthalate in a phosphate buffer solution was adjusted to pH 2.6 with citric acid. The substrate was immersed in the solution and heated at 80° C. for 30 minutes using the DKN602 Constant Temperature Oven (manufactured by Yamato Scientific Co., Ltd.). The molded body thus obtained was stationarily immersed in a phosphate buffer solution to be washed, and, after the phosphate buffer solution was replaced with a fresh phosphate buffer solution, the medical device was further heated in the autoclave at 121° C. for 30 minutes. The results of evaluating the obtained medical device using the above methods are shown in Tables 1 to 3.

Example 11

The molded body obtained in Manufacturing Example 1 was used as a substrate. An aqueous solution containing 0.19% by mass of an acrylic acid/N-vinylpyrrolidone/N,N-dimethylacrylamide copolymer (number ratio of basic group/acidic group: 0, molar ratio in copolymerization: 1/1/8, Mw: 600,000, manufactured by Osaka Organic Chemical Industry Ltd.) and 0.2% by mass of dipotassium glycyrrhizinate in a phosphate buffer solution was adjusted to pH 3.2 with citric acid. The substrate was immersed in the solution and heated at 80° C. for 30 minutes using the DKN602 Constant Temperature Oven (manufactured by Yamato Scientific Co., Ltd.). The medical device thus obtained was stationarily immersed in a phosphate buffer solution to be washed, and, after the phosphate buffer solution was replaced with a fresh phosphate buffer solution, the medical device was further heated in the autoclave at 121° C. for 30 minutes. The results of evaluating the obtained medical device using the above methods are shown in Tables 1 to 3.

Example 12

A commercially available hydrogel lens containing 2-hydroxyethyl methacrylate as a main component "1-Day Acuvue (registered trademark)" (etafilcon A, manufactured by Johnson & Johnson) was used as a substrate. An aqueous solution containing 0.18% by mass of an acrylic acid/2-hydroxyethyl methacrylate/N,N-dimethylacrylamide copolymer (number ratio of basic group/acidic group: 0, molar ratio in copolymerization: 1/1/2, Mw: 400,000, manufactured by Osaka Organic Chemical Industry Ltd.) and 0.2% by mass of dipotassium glycyrrhizinate hydrate in a phosphate buffer solution was adjusted to pH 3.2 with citric acid. The substrate was immersed in the solution and heated at 90° C. for 30 minutes using the DKN602 Constant Temperature Oven (manufactured by Yamato Scientific Co., Ltd.). The medical device thus obtained was stationarily immersed in a phosphate buffer solution to be washed, and, after the phosphate buffer solution was replaced with a fresh phosphate buffer solution, the medical device was further heated in the autoclave at 121° C. for 30 minutes. The results of evaluating the obtained medical device using the above methods are shown in Tables 1 to 3.

Example 13

A commercially available hard lens, "MENICON Z (registered trademark)" (manufactured by Menicon Co., Ltd.), containing a silicone component as a main component was used as a substrate. An aqueous solution containing 0.18% by mass of an acrylic acid/methoxy polyethylene glycol methacrylate/N,N-dimethylacrylamide copolymer (number ratio of basic group/acidic group: 0, molar ratio in copolymerization: 1/1/8, Mw: 700,000, manufactured by Osaka Organic Chemical Industry Ltd.) and 0.2% by mass of dipotassium glycyrrhizinate in a phosphate buffer solution was adjusted to pH 3.2 with citric acid. The substrate was immersed in the solution and heated at 85° C. for 30 minutes using the DKN602 Constant Temperature Oven (manufactured by Yamato Scientific Co., Ltd.). The medical device thus obtained was stationarily immersed in a phosphate buffer solution to be washed, and, after the phosphate buffer solution was replaced with a fresh phosphate buffer solution, the medical device was further heated in the autoclave at 121° C. for 30 minutes. The results of evaluating the obtained medical device using the above methods are shown in Tables 1 to 3.

Comparative Example 1

The results of evaluating a commercially available silicone hydrogel lens containing silicone as a main component "MyDay (registered trademark)" (stenfilcon A, manufactured by CooperVision Inc.) using the above methods are shown in Tables 1 to 3. Unmeasured items and items unmeasurable owing to use of commercially available products are denoted by "none" (the word "none" in Tables 1 to 3 has the same denotation).

Comparative Examples 2 to 5

An experiment was performed in the same manner as in Example 1 except that dipotassium glycyrrhizinate was changed to a compound shown in Table 1. The results of evaluating the obtained medical device (a hydrophilic polymer layer was not confirmed) using the above methods are shown in Tables 1 to 3.

Comparative Example 6

A commercially available silicone hydrogel lens containing silicone as a main component "MyDay (registered trademark)" (stenfilcon A, manufactured by CooperVision Inc.) was used as a substrate. An aqueous solution containing 0.19% by mass of an acrylic acid/acrylamide copolymer (number ratio of basic group/acidic group: 0, molar ratio in copolymerization: 7/93, Mw: 200,000, manufactured by oneself) in a phosphate buffer solution was adjusted to pH 3.2 with citric acid. The substrate was immersed in the solution, followed by heating in an autoclave at 121° C. for 30 minutes. The molded body thus obtained was immersed in a phosphate buffer solution to be washed for 30 seconds, and, after the phosphate buffer solution was replaced with a fresh phosphate buffer solution, the molded body was further heated in the autoclave at 121° C. for 30 minutes. The results of evaluating the obtained medical device (a hydrophilic polymer layer was not confirmed) using the above methods are shown in Tables 1 to 3.

Comparative Example 7

An experiment was performed in the same manner as in Comparative Example 6 except that the acrylic acid/acrylamide copolymer was changed to an acrylic acid/acrylamide copolymer (number ratio of basic group/acidic group: 0, molar ratio in copolymerization: 1/9, Mw: 200,000, manufactured by oneself). The results of evaluating the obtained medical device (a hydrophilic polymer layer was not confirmed) using the above methods are shown in Tables 1 to 3.

Comparative Example 8

An experiment was performed in the same manner as in Comparative Example 6 except that the acrylic acid/acrylamide copolymer was changed to an acrylic acid/acrylamide copolymer (number ratio of basic group/acidic group: 0, molar ratio in copolymerization: 3/7, Mw: 200,000, manufactured by oneself). The results of evaluating the obtained medical device (a hydrophilic polymer layer was not confirmed) using the above methods are shown in Tables 1 to 3.

Comparative Example 9

The molded body obtained in Manufacturing Example 1 was used as a substrate. An aqueous solution containing 0.1% by mass of an acrylic acid/vinylpyrrolidone copolymer (number ratio of basic group/acidic group: 0, molar ratio in copolymerization: 1/9, Mw: 400,000, manufactured by Osaka Organic Chemical Industry Ltd.) and 0.3% by mass of urea in pure water was adjusted to pH 3.8 with sulfuric acid. The substrate was immersed in the solution, followed by heating in an autoclave at 121° C. for 30 minutes. The molded body thus obtained was washed with a phosphate buffer solution under shaking at 250 rpm for 30 seconds. After replacing the phosphate buffer solution by a fresh phosphate buffer solution, the molded body was further heated in the autoclave at 121° C. for 30 minutes. The results of evaluating the obtained medical device (a hydrophilic polymer layer was not confirmed) using the above methods are shown in Tables 1 to 3.

Comparative Example 10

A commercially available silicone hydrogel lens containing polyvinylpyrrolidone and silicone as main components "1-Day Acuvue TruEye (registered trademark)" (narafilcon A, manufactured by Johnson & Johnson) was used as a substrate. An aqueous solution containing 0.2% by mass of an acrylic acid/N,N-dimethylacrylamide copolymer (number ratio of basic group/acidic group: 0, molar ratio in copolymerization: 1/9, Mw: 800,000, manufactured by Osaka Organic Chemical Industry Ltd.) and 0.3% by mass of urea in pure water was adjusted to pH 3.0 with sulfuric acid. The substrate was immersed in the solution, followed by heating in an autoclave at 121° C. for 30 minutes. The molded body thus obtained was washed with a phosphate buffer solution under shaking at 250 rpm for 30 seconds. After replacing the phosphate buffer solution by a fresh phosphate buffer solution, the molded body was further heated in the autoclave at 121° C. for 30 minutes. The results of evaluating the obtained medical device (a hydrophilic polymer layer was not confirmed) using the above methods are shown in Tables 1 to 3.

Comparative Example 11

The results of by evaluating a commercially available silicone hydrogel lens containing polyvinylpyrrolidone and silicone as main components "1-Day Acuvue TruEye (registered trademark)" (narafilcon A, manufactured by Johnson & Johnson) using the above methods are shown in Tables 1 to 3.

Comparative Example 12

The results of by evaluating, using the above methods, the molded body obtained in Manufacturing Example 1 are shown in Tables 1 to 3.

TABLE 1

| | Substrate | Moisture Content of Substrate (%) | Hydrophilic Polymer and Concentration Thereof in Solution | Compound Having Acidic Group and Ring Structure, and Concentration of the Compound | Initial pH | pH after Heat Treatment |
|---|---|---|---|---|---|---|
| Example 1 | "MyDay (registered trademark)" | 54 | 0.19% by mass Acrylic Acid/N,N-Dimethylacrylamide Copolymer | 0.2% by mass Dipotassium Glycyrrhizinate | 3.2 | 3.3 |
| Example 2 | "MyDay (registered trademark)" | 54 | | 0.2% by mass Dipotassium Glycyrrhizinate Hydrate | 3.2 | 3.3 |

TABLE 1-continued

| | Substrate | Moisture Content of Substrate (%) | Hydrophilic Polymer and Concentration Thereof in Solution | Compound Having Acidic Group and Ring Structure, and Concentration of the Compound | Initial pH | pH after Heat Treatment |
|---|---|---|---|---|---|---|
| Example 3 | "MyDay (registered trademark)" | 54 | | 0.2% by mass Pyridoxine Hydrochloride | 3.2 | 3.3 |
| Example 4 | "MyDay (registered trademark)" | 54 | | 0.2% by mass L-Histidine | 3.2 | 3.2 |
| Example 5 | "MyDay (registered trademark)" | 54 | | 0.2% by mass Sodium Benzoate | 3.2 | 3.3 |
| Example 6 | "MyDay (registered trademark)" | 54 | | 0.2% by mass Disodium Phthalate | 3.2 | 3.3 |
| Example 7 | "MyDay (registered trademark)" | 54 | | 0.2% by mass Disodium Terephthalate | 3.2 | 3.3 |
| Example 8 | "MyDay (registered trademark)" | 54 | | 0.2% by mass Dipotassium Glycyrrhizinate | 3.2 | 3.2 |
| Example 9 | "MyDay (registered trademark)" | 54 | | 0.2% by mass Sodium Benzoate | 2.6 | 2.6 |
| Example 10 | "MyDay (registered trademark)" | 54 | | 0.2% by mass Disodium Terephthalate | 2.6 | 2.6 |
| Example 11 | Manufacturing Example 1 | less than 1 | 0.19% by mass Acrylic Acid/N-Vinylpyrrolidone/N,N-Dimethylacrylamide Copolymer | 0.2% by mass Dipotassium Glycyrrhizinate | 3.2 | 3.3 |
| Example 12 | "1 day Acuvue (registered trademark)" | 58 | 0.18% by mass Acrylic Acid/2-Hydroxyethyl Methacrylate/N,N-Dimethylacrylamide Copolymer | 0.2% by mass Dipotassium Glycyrrhizinate Hydrate | 3.2 | 3.3 |
| Example 13 | "Menicon Z (registered trademark)" | less than 1 | 0.18% by mass Acrylic Acid/Methoxy Polyethylene Glycol Methacrylate/N,N-Dimethylacrylamide Copolymer | 0.2% by mass Dipotassium Glycyrrhizinate | 3.2 | 3.3 |
| Comparative Example 1 | "MyDay (registered trademark)" | 54 | none | none | none | none |
| Comparative Example 2 | "MyDay (registered trademark)" | 54 | 0.19% by mass Acrylic Acid/N,N-Dimethylacrylamide Copolymer | 0.2% by mass 1,2-Phenylenediamine Dihydrochloride | 2.5 | 2.6 |
| Comparative Example 3 | "MyDay (registered trademark)" | 54 | | 0.2% by mass 1,3-Phenylenediamine Dihydrochloride | 3.0 | 3.1 |
| Comparative Example 4 | "MyDay (registered trademark)" | 54 | | 0.2% by mass p-Toluidine Hydrochloride | 3.2 | 3.2 |
| Comparative Example 5 | "MyDay (registered trademark)" | 54 | | 0.05% by mass DL-Malic Acid | 3.2 | 3.2 |
| Comparative Example 6 | "MyDay (registered trademark)" | 54 | 0.19% by mass Acrylic Acid/Acrylamide Copolymer | none | 3.2 | 3.3 |
| Comparative Example 7 | "MyDay (registered trademark)" | 54 | 0.19% by mass Acrylic Acid/Acrylamide Copolymer | none | 3.2 | 3.3 |
| Comparative Example 8 | "MyDay (registered trademark)" | 54 | 0.19% by mass Acrylic Acid/Acrylamide Copolymer | none | 3.2 | 3.4 |
| Comparative Example 9 | Manufacturing Example 1 | less than 1 | 0.1% by mass Acrylic Acid/Vinylpyrrolidone Copolymer | none (0.3% by mass Urea instead) | 3.8 | 7.0 |
| Comparative Example 10 | "1 day AcuvueTruEye (registered trademark)" | 46 | 0.2% by mass Acrylic Acid/N,N-Dimethylacrylamide Copolymer | none (0.3% by mass Urea instead) | 3.0 | 7.0 |
| Comparative Example 11 | "1 day AcuvueTruEye (registered trademark)" | 46 | none | none | none | none |
| Comparative Example 12 | Manufacturing Example 1 | less than 1 | none | none | none | none |

TABLE 2

| | Liquid Film Retention Time (second) | Lubricity | Moisture Content of Medical Device (%) | Elemental Composition Analysis Results of Hydrophilic Polymer Layer | Thickness of Hydrophilic Polymer Layer (nm) | Moisture Content Change Rate of Substrate and Moisture Content Change Rate of Device | Friction Coefficient |
|---|---|---|---|---|---|---|---|
| Example 1 | A (120 seconds) | C | 54.5 | Hydrophilic Polymer Separated into Two Layers (One Thereof Mixed with Substrate) | 13 | 0.5 | 0.107 |
| Example 2 | A (120 seconds) | C | 54.3 | Hydrophilic Polymer Separated into Two Layers | 10 | 0.3 | 0.116 |

TABLE 2-continued

| | Liquid Film Retention Time (second) | Lubricity | Moisture Content of Medical Device (%) | Elemental Composition Analysis Results of Hydrophilic Polymer Layer | Thickness of Hydrophilic Polymer Layer (nm) | Moisture Content Change Rate of Substrate and Moisture Content Change Rate of Device | Friction Coefficient |
|---|---|---|---|---|---|---|---|
| Example 3 | B (17 seconds) | C | 54.6 | Hydrophilic Polymer Separated into Two Layers (One Thereof Mixed with Substrate) | 8 | 0.6 | 0.171 |
| Example 4 | B (15 seconds) | C | 54.2 | Hydrophilic Polymer Separated into Two Layers (One Thereof Mixed with Substrate) | 8 | 0.2 | 0.176 |
| Example 5 | B (16 seconds) | C | 54.1 | Hydrophilic Polymer Separated into Two Layers (One Thereof Mixed with Substrate) | 7 | 0.1 | 0.18 |
| Example 6 | B (17 seconds) | C | 55.0 | Hydrophilic Polymer Separated into Two Layers (One Thereof Mixed with Substrate) | 8 | 1 | 0.172 |
| Example 7 | B (15 seconds) | C | 55.1 | Hydrophilic Polymer Partially Mixed with Substrate | 9 | 1.1 | 0.189 |
| Example 8 | A (28 seconds) | C | 54.5 | Hydrophilic Polymer Partially Mixed with Substrate | 10 | 0.5 | 0.17 |
| Example 9 | B (15 seconds) | C | 54.7 | Hydrophilic Polymer Partially Mixed with Substrate | 9 | 0.7 | 0.168 |
| Example 10 | B (16 seconds) | C | 54.8 | Hydrophilic Polymer Partially Mixed with Substrate | 9 | 0.8 | 0.161 |
| Example 11 | B (15 seconds) | C | less than 1 | Hydrophilic Polymer Partially Mixed with Substrate | 8 | less than 1 | 0.163 |
| Example 12 | A (120 seconds) | C | 58.5 | Hydrophilic Polymer Partially Mixed with Substrate | 10 | 0.5 | 0.188 |
| Example 13 | B (16 seconds) | C | less than 1 | Hydrophilic Polymer Partially Mixed with Substrate | 7 | less than 1 | 0.183 |
| Comparative Example 1 | D (2 seconds) | C | none | Hydrophilic Polymer Layer not Confirmed | 0 | none | 0.235 |
| Comparative Example 2 | D (1 second) | C | 54 | Hydrophilic Polymer Layer not Confirmed | 0 | 0 | 0.249 |
| Comparative Example 3 | D (3 seconds) | C | 54.1 | Hydrophilic Polymer Layer not Confirmed | 0 | 0.1 | 0.241 |
| Comparative Example 4 | D (1 second) | C | 54.2 | Hydrophilic Polymer Layer not Confirmed | 0 | 0.2 | 0.247 |
| Comparative Example 5 | D (1 second) | C | 54.1 | Hydrophilic Polymer Layer not Confirmed | 0 | 0.1 | 0.243 |
| Comparative Example 6 | D (3 seconds) | C | 54 | Hydrophilic Polymer Layer not Confirmed | 0 | 0 | 0.277 |
| Comparative Example 7 | D (4 seconds) | C | 54 | Hydrophilic Polymer Layer not Confirmed | 0 | 0 | 0.218 |
| Comparative Example 8 | D (3 seconds) | C | 54 | Hydrophilic Polymer Layer not Confirmed | 0 | 0 | 0.377 |
| Comparative Example 9 | D (1 second) | E | less than 1 | Hydrophilic Polymer Layer not Confirmed | 0 | 0 | 0.83 |
| Comparative Example 10 | D (2 seconds) | C | 46 | Hydrophilic Polymer Layer not Confirmed | 0 | 0 | 0.105 |
| Comparative Example 11 | D (3 seconds) | C | 46 | Hydrophilic Polymer Layer not Confirmed | 0 | 0 | 0.19 |
| Comparative Example 12 | E (less than 1 second) | E | less than 1 | Hydrophilic Polymer Layer not Confirmed | 0 | 0 | 0.85 |

TABLE 3

| | Lipid Deposition Amount | Tensile Elastic Modulus of Substrate (MPa) | Tensile Elastic Modulus of Medical Device (MPa) | Tensile Elastic Modulus Change Rate due to Formation of Hydrophilic Polymer Layer (%) | Size of Substrate (mm) | Size of Medical Device (mm) | Size Change Rate due to Formation of Hydrophilic Polymer Layer (%) |
|---|---|---|---|---|---|---|---|
| Example 1 | No Deposition | 0.61 | 0.61 | 0.2 | 14.2 | 14.13 | −0.5 |
| Example 2 | No Deposition | 0.61 | 0.60 | −0.9 | 14.2 | 14.14 | −0.4 |
| Example 3 | No Deposition | 0.61 | 0.61 | 0.7 | 14.2 | 14.12 | −0.6 |
| Example 4 | No Deposition | 0.61 | 0.62 | 1.4 | 14.2 | 14.16 | −0.3 |

TABLE 3-continued

| | Lipid Deposition Amount | Tensile Elastic Modulus of Substrate (MPa) | Tensile Elastic Modulus of Medical Device (MPa) | Tensile Elastic Modulus Change Rate due to Formation of Hydrophilic Polymer Layer (%) | Size of Substrate (mm) | Size of Medical Device (mm) | Size Change Rate due to Formation of Hydrophilic Polymer Layer (%) |
|---|---|---|---|---|---|---|---|
| Example 5 | No Deposition | 0.61 | 0.61 | 0.1 | 14.2 | 14.18 | −0.1 |
| Example 6 | No Deposition | 0.61 | 0.61 | 0.8 | 14.2 | 14.15 | −0.4 |
| Example 7 | No Deposition | 0.61 | 0.62 | 2.0 | 14.2 | 14.18 | −0.1 |
| Example 8 | No Deposition | 0.61 | 0.60 | −0.9 | 14.2 | 14.15 | −0.4 |
| Example 9 | No Deposition | 0.61 | 0.61 | 0.8 | 14.2 | 14.17 | −0.2 |
| Example 10 | No Deposition | 0.61 | 0.62 | 1.5 | 14.2 | 14.15 | −0.4 |
| Example 11 | No Deposition | 0.53 | 0.53 | 0.1 | 14.0 | 14.10 | 0.7 |
| Example 12 | No Deposition | 0.30 | 0.29 | −3.3 | 14.2 | 13.9 | −2.1 |
| Example 13 | No Deposition | unmeasured owing to test piece being unable to be cut out | unmeasured owing to test piece being unable to be cut out | unmeasured owing to test piece being unable to be cut out | 8.4 | 8.4 | 0 |
| Comparative Example 1 | Deposited on ⅓ of Entire Area | 0.61 | none | none | 14.2 | none | none |
| Comparative Example 2 | Deposited on ⅓ of Entire Area | 0.61 | 0.60 | −0.9 | 14.2 | 14.2 | 0 |
| Comparative Example 3 | Deposited on ⅓ of Entire Area | 0.61 | 0.61 | 0.1 | 14.2 | 14.19 | −0.1 |
| Comparative Example 4 | Deposited on ⅓ of Entire Area | 0.61 | 0.61 | 0.3 | 14.2 | 14.18 | −0.1 |
| Comparative Example 5 | Deposited on ⅓ of Entire Area | 0.61 | 0.62 | 1.4 | 14.2 | 14.15 | −0.4 |
| Comparative Example 6 | Deposited on ⅓ of Entire Area | 0.61 | 0.61 | 0.2 | 14.2 | 14.19 | −0.1 |
| Comparative Example 7 | Deposited on ⅓ of Entire Area | 0.61 | 0.61 | 0.2 | 14.2 | 14.2 | 0 |
| Comparative Example 8 | Deposited on ⅓ of Entire Area | 0.61 | 0.61 | 0.2 | 14.2 | 14.2 | 0 |
| Comparative Example 9 | Deposited on Entire Area | 0.53 | 0.49 | −6.8 | 14 | 14 | 0 |
| Comparative Example 10 | Deposited on ⅓ of Entire Area | 0.70 | 0.71 | 0.4 | 14.2 | 14.1 | −0.7 |
| Comparative Example 11 | Deposited on ⅓ of Entire Area | 0.70 | none | none | 14.2 | none | none |
| Comparative Example 12 | Deposited on Entire Area | 0.53 | none | none | 14.0 | none | none |

The invention claimed is:

1. A method for manufacturing a medical device including a substrate and a hydrophilic polymer layer, said method comprising the steps of:
    disposing said substrate in a solution having an initial pH of 2.0 or higher and 6.0 or lower; and
    heating said solution;
    wherein said solution contains:
        a hydrophilic polymer having an acidic group;
        a compound having an acidic group and a ring structure; and
        an organic acid;
    wherein said compound having the acidic group and the ring structure is a compound selected from dipotassium glycyrrhizinate, dipotassium glycyrrhizinate hydrate, pyridoxine hydrochloride, L-histidine, phenol, catechol, resorcinol, sodium benzoate, disodium phthalate, and disodium terephthalate; and
    wherein said organic acid is selected from the group consisting of acetic acid, citric acid, formic acid, ascorbic acid, trifluoromethanesulfonic acid, methanesulfonic acid, propionic acid, butyric acid, glycolic acid, lactic acid and malic acid.

2. The method for manufacturing a medical device according to claim 1, wherein said solution further contains a low-molecular-weight acid having no ring structure.

3. The method for manufacturing a medical device according to claim 2, wherein said low-molecular-weight acid having no ring structure is an organic acid.

4. The method for manufacturing the medical device according to claim 1, wherein the step of heating said solution is a step of heating said solution in the range of from 50° C. to 100° C.

5. The method according to claim 1, wherein the thickness of said hydrophilic polymer layer in a dry state after said heating is in the range of from 1 nm or more and less than 100 nm, as measured by observation using a scanning transmission electron microscope.

6. The method according to claim 1, wherein said medical device is an ophthalmic lens, a dermal covering material, a wound dressing material, a skin protection material, a skin medicine carrier, an infusion tube, a gas delivery tube, a drainage tube, a blood circuit, a covering tube, a catheter, a stent, a sheath, a biosensor chip, or an endoscopic covering material.

7. The method according to claim 1, wherein said medical device is a contact lens.

* * * * *